(12) United States Patent
Cooreman et al.

(10) Patent No.: US 8,012,477 B2
(45) Date of Patent: Sep. 6, 2011

(54) METHODS OF TREATING MULTIPLE MYELOMA USING IL-17 BINDING MOLECULES

(75) Inventors: Michael Cooreman, Randolph, NJ (US); Franco E. Di Padova, Birsfelden (CH)

(73) Assignees: Novartis AG, Basel (CH); Novartis Pharma GmbH, Vienna (AT)

( * ) Notice: Subject to any disclaimer, the term of this patent is extended or adjusted under 35 U.S.C. 154(b) by 398 days.

(21) Appl. No.: 12/223,050

(22) PCT Filed: Jan. 30, 2007

(86) PCT No.: PCT/US2007/061276
§ 371 (c)(1),
(2), (4) Date: Jul. 21, 2008

(87) PCT Pub. No.: WO2007/117749
PCT Pub. Date: Oct. 18, 2007

(65) Prior Publication Data
US 2010/0266608 A1 Oct. 21, 2010

Related U.S. Application Data

(60) Provisional application No. 60/763,673, filed on Jan. 31, 2006.

(51) Int. Cl.
*A61K 39/00* (2006.01)
*A61K 39/395* (2006.01)

(52) U.S. Cl. ............ 424/133.1; 530/388.23; 530/388.15; 530/387.3; 530/351

(58) Field of Classification Search ........................ None
See application file for complete search history.

(56) References Cited

FOREIGN PATENT DOCUMENTS

| WO | 00/69463 | 11/2000 |
|---|---|---|
| WO | WO 2006/013107 | 2/2006 |
| WO | WO 2006/054059 | 5/2006 |

OTHER PUBLICATIONS

Benchetrit et al. Interleukin-17 inhibits tumor cell growth by means of a T-cell-dependent mechanism. Blood, Mar. 15, 2002, vol. 99, No. 6, pp. 2114-2121.*
Wróbel et al. Interleukin-17 in acute myeloid leukemia. J Cell Mol Med. Oct.-Dec. 2003;7(4):472-4.*
Fan et al. The prevalence of Th17 cells in patients with acute myeloid leukemia. Zhonghua Xue Ye Xue Za Zhi. Sep. 2010;31(9):617-620 (abstrac).*
Numasaki et al. "Interleukin-17 promotes angiogenesis and tumor growth", Blood, vol. 101, No. 7, pp. 2620-2627, Apr. 1, 2003.
Dumont F J: "IL-17 cytokine/receptor families: Emerging targets for the modulation of inflammatory responses", Expert Opinion On Therapeutic Patents, vol. 13, No. 3, pp. 287-303, (2003).
R&D Systems: "Monoclonal Anti-human IL-17 Antibody", Product Data Sheet, pp. 1-2, (2004).
Prabhala et al., "Elevated IL-17 produced by TH17 cells promotes myeloma cell growth and inhibits immune function in multiple myeloma", Blood, vol. 115, pp. 5385-5392, (2010).
Prabhala et al., (2010), Abstract #456, "Human Monoclona Antibody Targeting IL-17A (AIN457) Down-Regulates MM Cell-Growth and Survival and Inhibits Osteoclast Development In Vitro and In Vivo: A Potential Novel Therapeutic Application in Myeloma", presented Monday Dec. 6, 2010 at the 52$^{nd}$ ASH Annual Meeting and Exposition in Orlando Florida.

* cited by examiner

*Primary Examiner* — Dong Jiang
(74) *Attorney, Agent, or Firm* — Leslie Fischer

(57) ABSTRACT

An IL-17 binding molecule, in particular an antibody to human IL-17, more preferably a human antibody to human IL-17 is provided, wherein the hypervariable regions of the heavy and light chains have amino acid sequences as defined, for use in the treatment of a solid or hematological malignant diseases.

6 Claims, No Drawings

SEQUENCE LISTING

<160> NUMBER OF SEQ ID NOS: 13

<210> SEQ ID NO 1
<211> LENGTH: 5
<212> TYPE: PRT
<213> ORGANISM: artificial
<220> FEATURE:
<223> OTHER INFORMATION: CDR1 region of AIN457
<220> FEATURE:
<221> NAME/KEY: DOMAIN
<222> LOCATION: (1)..(5)
<223> OTHER INFORMATION: CDR1 = hypervariable region 1 of heavy chain of
      AIN457

<400> SEQUENCE: 1

Asn Tyr Trp Met Asn
1               5

<210> SEQ ID NO 2
<211> LENGTH: 17
<212> TYPE: PRT
<213> ORGANISM: artificial
<220> FEATURE:
<223> OTHER INFORMATION: CDR2 of AIN457
<220> FEATURE:
<221> NAME/KEY: DOMAIN
<222> LOCATION: (1)..(17)
<223> OTHER INFORMATION: CDR2 = hypervariable region 2 of heavy chain of
      AIN457

<400> SEQUENCE: 2

Ala Ile Asn Gln Asp Gly Ser Glu Lys Tyr Tyr Val Gly Ser Val Lys
1               5                   10                  15

Gly

<210> SEQ ID NO 3
<211> LENGTH: 18
<212> TYPE: PRT
<213> ORGANISM: artificial
<220> FEATURE:
<223> OTHER INFORMATION: CDR3 of AIN457
<220> FEATURE:
<221> NAME/KEY: DOMAIN
<222> LOCATION: (1)..(18)
<223> OTHER INFORMATION: CDR3 = hypervariable region 3 of heavy chain of
      AIN457

<400> SEQUENCE: 3

Asp Tyr Tyr Asp Ile Leu Thr Asp Tyr Tyr Ile His Tyr Trp Tyr Phe
1               5                   10                  15

Asp Leu

<210> SEQ ID NO 4
<211> LENGTH: 12
<212> TYPE: PRT
<213> ORGANISM: artificial
<220> FEATURE:
<223> OTHER INFORMATION: CDR1' of AIN457
<220> FEATURE:
<221> NAME/KEY: DOMAIN
<222> LOCATION: (1)..(12)
<223> OTHER INFORMATION: CDR1' = hypervariable region 1 of light chain
      of AIN457

<400> SEQUENCE: 4

Arg Ala Ser Gln Ser Val Ser Ser Ser Tyr Leu Ala
1               5                   10

```
<210> SEQ ID NO 5
<211> LENGTH: 7
<212> TYPE: PRT
<213> ORGANISM: artificial
<220> FEATURE:
<223> OTHER INFORMATION: CDR2' of AIN457
<220> FEATURE:
<221> NAME/KEY: DOMAIN
<222> LOCATION: (1)..(7)
<223> OTHER INFORMATION: CDR2' = hypervariable region 2 of light chain
      AIN457

<400> SEQUENCE: 5

Gly Ala Ser Ser Arg Ala Thr
1               5

<210> SEQ ID NO 6
<211> LENGTH: 9
<212> TYPE: PRT
<213> ORGANISM: artificial
<220> FEATURE:
<223> OTHER INFORMATION: CDR3' of AIN457
<220> FEATURE:
<221> NAME/KEY: DOMAIN
<222> LOCATION: (1)..(9)
<223> OTHER INFORMATION: CDR3' = hypervariable region 3 of light chain
      AIN457

<400> SEQUENCE: 6

Gln Gln Tyr Gly Ser Ser Pro Cys Thr
1               5

<210> SEQ ID NO 7
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: DNA of heavy chain domain of AIN457

<400> SEQUENCE: 7 gag gtg cag ttg gtg gag tct ggg gga ggc ttg gtc cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agt aac tat      96
Ser Leu Arg Leu Ser Cys Ala Ala Ser Gly Phe Thr Phe Ser Asn Tyr
                20                  25                  30 tgg atg aac tgg gtc cgc cag gct cca ggg aaa ggg ctg gag tgg gtg     144
Trp Met Asn Trp Val Arg Gln Ala Pro Gly Lys Gly Leu Glu Trp Val
            35                  40                  45 gcc gcc ata aac caa gat gga agt gag aaa tac tat gtg ggc tct gtg     192
Ala Ala Ile Asn Gln Asp Gly Ser Glu Lys Tyr Tyr Val Gly Ser Val
        50                  55                  60 aag ggc cga ttc acc atc tcc aga gac aac gcc aag aac tca ctg tat     240
Lys Gly Arg Phe Thr Ile Ser Arg Asp Asn Ala Lys Asn Ser Leu Tyr
65                  70                  75                  80 ctg caa atg aac agc ctg aga gtc gag gac acg gct gtg tat tac tgt     288
Leu Gln Met Asn Ser Leu Arg Val Glu Asp Thr Ala Val Tyr Tyr Cys
                85                  90                  95 gtg agg gac tat tac gat att ttg act gat tat tac atc cac tat tgg     336
Val Arg Asp Tyr Tyr Asp Ile Leu Thr Asp Tyr Tyr Ile His Tyr Trp
                100                 105                 110 tac ttc gat ctc tgg ggc cgt ggc acc ctg gtc act gtc tcc tca         381
Tyr Phe Asp Leu Trp Gly Arg Gly Thr Leu Val Thr Val Ser Ser
            115                 120                 125
```

```
<210> SEQ ID NO 8
<211> LENGTH: 127
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125

<210> SEQ ID NO 9
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: DNA of varibale part of light chain of AIN457

<400> SEQUENCE: 9 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca ccg     288
Pro Glu Asp Phe Ala Val Tyr Tyr Cys Gln Gln Tyr Gly Ser Ser Pro
                85                  90                  95 tgc acc ttc ggc caa ggg aca cga ctg gag att aaa cga                 327
Cys Thr Phe Gly Gln Gly Thr Arg Leu Glu Ile Lys Arg
            100                 105

<210> SEQ ID NO 10
<211> LENGTH: 109
<212> TYPE: PRT
<213> ORGANISM: Homo sapiens

<400> SEQUENCE: 10
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
            100                 105
```

```
<210> SEQ ID NO 11
<211> LENGTH: 10
<212> TYPE: PRT
<213> ORGANISM: artificial
<220> FEATURE:
<223> OTHER INFORMATION: CDR1-x of AIN457
<220> FEATURE:
<221> NAME/KEY: DOMAIN
<222> LOCATION: (1)..(10)
<223> OTHER INFORMATION: CDR1-x = hypervariable domain x of heavy chain
      of AIN457

<400> SEQUENCE: 11

Gly Phe Thr Phe Ser Asn Tyr Trp Met Asn
1               5                   10

<210> SEQ ID NO 12
<211> LENGTH: 11
<212> TYPE: PRT
<213> ORGANISM: artificial
<220> FEATURE:
<223> OTHER INFORMATION: CDR2-x of AIN457
<220> FEATURE:
<221> NAME/KEY: domain
<222> LOCATION: (1)..(11)
<223> OTHER INFORMATION: CDR2-x = hypervariable domain of heavy chain x
      of AIN457

<400> SEQUENCE: 12

Ala Ile Asn Gln Asp Gly Ser Glu Lys Tyr Tyr
1               5                   10

<210> SEQ ID NO 13
<211> LENGTH: 23
<212> TYPE: PRT
<213> ORGANISM: artificial
<220> FEATURE:
<223> OTHER INFORMATION: CDR3-x of AIN457
<220> FEATURE:
<221> NAME/KEY: domain
<222> LOCATION: (1)..(23)
<223> OTHER INFORMATION: CDR3-x = hypervariable domain x of heavy chain
      AIN457

<400> SEQUENCE: 13

Cys Val Arg Asp Tyr Tyr Asp Ile Leu Thr Asp Tyr Tyr Ile His Tyr
1               5                   10                  15

Trp Tyr Phe Asp Leu Trp Gly
                20
```

METHODS OF TREATING MULTIPLE MYELOMA USING IL-17 BINDING MOLECULES

This application is a 371 of PCT/US2007/061276 filed on Jan. 30, 2007, which claims benefit of U.S. Provisional Application No. 60/763,673, filed Jan. 31, 2006, which in their entirety are herein incorporated by reference.

The present invention relates to immunotherapy and more particularly provides the use of an IL-17 binding molecules in the treatment of a proliferative disease and in particular of solid malignant proliferative diseases or hematological proliferative diseases.

IL-17, a T-cell derived cytokine present e.g. in rheumatoid arthritis (RA), acts as a pro-inflammatory cytokine, particularly in conjunction with IL-1 and TNF-α, and blockage of IL-1 and IL-17 has a synergistic effect on inflammation and bone destruction in vivo. Inappropriate or excessive production of IL-17 is associated with the pathology of various diseases and disorders, such as rheumatoid arthritis, osteoarthritis, loosening of bone implants, acute transplant rejection, septicemia, septic or endotoxic shock, allergies, asthma, bone loss, psoriasis, ischemia, systemic sclerosis, stroke, and other inflammatory disorders. Antibodies to IL-17 have been proposed for use in the treatment of IL-17 mediated diseases and disorders; see for instance, WO 95/18826 and the discussion in the introduction thereof.

It has now been found in accordance with the present invention that IL-17 binding molecules are useful in inhibiting the growth of certain solid and hematological malignant diseases. Accordingly in a first aspect, the present invention provides the use of an IL-17 binding molecule in the treatment of a proliferative disease, such as cancer and in particular of solid malignant proliferative diseases or hematological malignant proliferative diseases.

Preferably an IL-17 binding molecule is used as described in PCT application PCT/EP2005/008470, which is herewith incorporated by reference, comprising at least one antigen binding site comprising an IL-17 binding molecule which comprises an antigen binding site comprising at least one immunoglobulin heavy chain variable domain ($V_H$) which comprises in sequence hypervariable regions CDR1, CDR2 and CDR3, said CDR1 having the amino acid sequence SEQ ID NO: 1 (N-Y-W-M-N), said CDR2 having the amino acid sequence SEQ ID NO: 2 (A-I-N-Q-D-G-S-E-K-Y-Y-V-G-S-V-K-G), and said CDR3 having the amino acid sequence SEQ ID NO: 3 (D-Y-Y-D-I-L-T-D-Y-Y-I-H-Y-W-Y-F-D-L); or direct CDR equivalents thereof.

In a preferred embodiment, the IL-17 binding molecule comprises at least one immunoglobulin light chain variable domain ($V_L$) which comprises in sequence hypervariable regions CDR1', CDR2' and CDR3', said CDR1' having the amino acid sequence SEQ ID NO: 4 (R-A-S-Q-S-V-S-S-S-Y-L-A), said CDR2' having the amino acid sequence SEQ ID NO: 5 (G-A-S-S-R-A-T) and said CDR3' having the amino acid sequence SEQ ID NO: 6 (Q-Q-Y-G-S-S-P-C-T) or direct CDR' equivalents thereof.

In another preferred embodiment, the IL-17 binding molecule comprises an antigen binding site comprising at least one immunoglobulin heavy chain variable domain ($V_H$) which comprises in sequence hypervariable regions CDR1-x, CDR2-x and CDR3-x, said CDR1-x having the amino acid sequence SEQ ID NO: 11 (G-F-T-F-S-N-Y-W-M-N), said CDR2-x having the amino acid sequence SEQ ID NO: 12 (A-I-N-Q-D-G-S-E-K-Y-Y), and said CDR3-x having the amino acid sequence SEQ ID NO: 13 (C-V-R-D-Y-Y-D-I-L-T-D-Y-Y-I-H-Y-W-Y-F-D-L-W-G); or direct CDR-x equivalents thereof.

Furthermore, in a preferred embodiment the IL-17 binding molecule comprises both heavy ($V_H$) and light chain ($V_L$) variable domains; said IL-17 binding molecule comprises at least one antigen binding site comprising:
  a) an immunoglobulin heavy chain variable domain ($V_H$) which comprises in sequence hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3 or direct CDR equivalents thereof; and
  b) an immunoglobulin light chain variable domain ($V_L$) which comprises in sequence hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6 or direct CDR' equivalents thereof.

Moreover, the IL-17 binding molecule may also comprise both heavy ($V_H$) and light chain ($V_L$) variable domains; said IL-17 binding molecule comprises at least one antigen binding site comprising:
  a) an immunoglobulin heavy chain variable domain ($V_H$) which comprises in sequence hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13 or direct CDR-x equivalents thereof; and
  b) an immunoglobulin light chain variable domain ($V_L$) which comprises in sequence hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6 or direct CDR' equivalents thereof.

Unless otherwise indicated, any polypeptide chain is herein described as having an amino acid sequence starting at the N-terminal extremity and ending at the C-terminal extremity. When the antigen binding site comprises both the $V_H$ and $V_L$ domains, these may be located on the same polypeptide molecule or, preferably, each domain may be on a different chain, the $V_H$ domain being part of an immunoglobulin heavy chain or fragment thereof and the $V_L$ being part of an immunoglobulin light chain or fragment thereof.

By "IL-17 binding molecule" is meant any molecule capable of binding to the IL-17 antigen either alone or associated with other molecules. The binding reaction may be shown by standard methods (qualitative assays) including, for example, a binding assay, competition assay or a bioassay for determining the inhibition of IL-17 binding to its receptor or any kind of binding assays, with reference to a negative control test in which an antibody of unrelated specificity but of the same isotype, e.g. an anti-CD25 antibody, is used.

Examples of antigen binding molecules include antibodies as produced by B-cells or hybridomas and chimeric, CDR-grafted or human antibodies or any fragment thereof, e.g. F(ab')$_2$ and Fab fragments, as well as single chain or single domain antibodies.

A single chain antibody consists of the variable domains of the heavy and light chains of an antibody covalently bound by a peptide linker usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By "chimeric antibody" is meant an antibody in which the constant regions of heavy or light chains or both are of human origin while the variable domains of both heavy and light chains are of non-human (e.g. murine) origin or of human origin but derived from a different human antibody. By "CDR-grafted antibody" is meant an antibody in which the hypervariable regions (CDRs) are derived from a donor antibody, such as a non-human (e.g. murine) antibody or a different human antibody, while all or substantially all the other parts of the immunoglobulin e.g. the constant regions and the highly conserved parts of the variable domains, i.e. the framework regions, are derived from an acceptor antibody, e.g. an antibody of human origin. A CDR-grafted antibody may however contain a few amino acids of the donor sequence in the framework regions, for instance in the parts of the framework regions adjacent to the hypervariable regions. By "human antibody" is meant an antibody in which the constant and variable regions of both the heavy and light chains are all of human origin, or substantially identical to sequences of human origin, not necessarily from the same antibody and includes antibodies produced by mice in which the murine immunoglobulin variable and constant part genes have been replaced by their human counterparts, e.g. as described in general terms in EP 0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770, 429, EP 0 438-474 B1 and EP 0 463151 B1.

Particularly preferred IL-17 binding molecules of the invention are human antibodies, especially the AIN457 antibody as described in Examples 1 and 2 of PCT/EP2005/008470.

Thus in preferred chimeric antibodies the variable domains of both heavy and light chains are of human origin, for instance those of the AIN457 antibody which are shown in SEQ ID NO: 10 (=variable domain of light chain, i.e. amino acid 1 to 109 of SEQ ID NO: 10) and SEQ ID NO: 8 (=variable domain of heavy chain, i.e. amino acid 1 to 127 of SEQ ID NO: 8). The constant region domains preferably also comprise suitable human constant region domains, for instance as described in "Sequences of Proteins of Immunological Interest", Kabat E. A. et al, US Department of Health and Human Services, Public Health Service, National Institute of Health.

Hypervariable regions may be associated with any kind of framework regions, though preferably are of human origin. Suitable framework regions are described in Kabat E. A. et al, ibid. The preferred heavy chain framework is a human heavy chain framework, for instance that of the AIN457 antibody. It consists in sequence e.g. of FR1 (amino acid 1 to 30 of SEQ ID NO: 8), FR2 (amino acid 36 to 49 of SEQ ID NO: 8), FR3 (amino acid 67 to 98 of SEQ ID NO: 8) and FR4 (amino acid 117 to 127 of SEQ ID NO: 8) regions. Taking into consideration the determined hypervariable regions of AIN457 by X-ray analysis, another preferred heavy chain framework consists in sequence of FR1-x (amino acid 1 to 25 of SEQ ID NO: 8), FR2-x (amino acid 36 to 49 of SEQ ID NO: 8), FR3-x (amino acid 61 to 95 of SEQ ID NO: 8) and FR4 (amino acid 119 to 127 of SEQ ID NO: 8) regions. In a similar manner, the light chain framework consists, in sequence, of FR1' (amino acid 1 to 23 of SEQ ID NO: 10), FR2' (amino acid 36 to 50 of SEQ ID NO: 10), FR3' (amino acid 58 to 89 of SEQ ID NO: 10) and FR4' (amino acid 99 to 109 of SEQ ID NO: 10) regions.

An IL-17 binding molecule according to the invention comprises at least one antigen binding site comprising either a first domain having an amino acid sequence substantially identical to that shown in SEQ ID NO: 8 starting with the amino acid at position 1 and ending with the amino acid at position 127 or a first domain as described above and a second domain having an amino acid sequence substantially identical to that shown in SEQ ID NO: 10, starting with the amino acid at position 1 and ending with the amino acid at position 109.

Monoclonal antibodies raised against a protein naturally found in all humans are typically developed in a non-human system e.g. in mice, and as such are typically non-human proteins. As a direct consequence of this, a xenogenic antibody as produced by a hybridoma, when administered to humans, elicits an undesirable immune response which is predominantly mediated by the constant part of the xenogenic immunoglobulin. This clearly limits the use of such antibodies as they cannot be administered over a prolonged period of time. Therefore it is particularly preferred to use single chain, single domain, chimeric, CDR-grafted, or especially human antibodies which are not likely to elicit a substantial allogenic response when administered to humans.

In view of the foregoing, a more preferred IL-17 binding molecule of the invention is selected from a human anti IL-17 antibody which comprises at least
a) an immunoglobulin heavy chain or fragment thereof which comprises (i) a variable domain comprising in sequence the hypervariable regions CDR1, CDR2 and CDR3 or direct CDR equivalents thereof and (ii) the constant part or fragment thereof of a human heavy chain; said CDR1 having the amino acid sequence SEQ ID NO: 1, said CDR2 having the amino acid sequence SEQ ID NO: 2, and said CDR3 having the amino acid sequence SEQ ID NO: 3; and
b) an immunoglobulin light chain or fragment thereof which comprises (i) a variable domain comprising in sequence the hypervariable regions and optionally also the CDR1', CDR2', and CDR3' hypervariable regions or direct CDR' equivalents thereof and (ii) the constant part or fragment thereof of a human light chain, said CDR1' having the amino acid sequence SEQ ID NO: 4, said CDR2' having the amino acid sequence SEQ ID NO: 5, and said CDR3' having the amino acid sequence SEQ ID NO: 6.

Alternatively, an IL-17 binding molecule according to the invention may be selected from a single chain binding molecule which comprises an antigen binding site comprising
a) a first domain comprising in sequence the hypervariable regions CDR1, CDR2 and CDR3 or direct CDR equivalents thereof, said CDR1 having the amino acid sequence SEQ ID NO: 1, said CDR2 having the amino acid sequence SEQ ID NO: 2, and said CDR3 having the amino acid sequence SEQ ID NO: 3; and
b) a second domain comprising the hypervariable regions CDR1', CDR2' and CDR3' or direct CDR' equivalents thereof, said CDR1' having the amino acid sequence SEQ ID NO: 4, said CDR2' having the amino acid sequence SEQ ID NO: 5, and said CDR3' having the amino acid sequence SEQ ID NO: 6; and
c) a peptide linker which is bound either to the N-terminal extremity of the first domain and to the C-terminal extremity of the second domain or to the C-terminal extremity of the first domain and to the N-terminal extremity of the second domain.

As it is well known, minor changes in an amino acid sequence such as deletion, addition or substitution of one, a few or even several amino acids may lead to an allelic form of the original protein which has substantially identical properties.

Thus, by the term "direct CDR equivalents thereof" are meant IL-17 binding molecules comprising in sequence the hypervariable regions $CDR1_i$, $CDR2_i$, and $CDR3_i$, (instead of CDR1, CDR2, and CDR3), wherein
  (i) the hypervariable region $CDR1_i$ differs by 3, preferably 2, more preferably 1 amino acid(s) from the hypervariable region CDR1 as shown in SEQ ID NO: 1; and
  (ii) the hypervariable region $CDR2_i$ differs by 3, preferably 2, more preferably 1 amino acid(s) from the hypervariable region CDR2 as shown in SEQ ID NO: 2; and
  (iii) the hypervariable region $CDR3_i$ differs by 3, preferably 2, more preferably 1 amino acid(s) from the hypervariable region CDR3 as shown in SEQ ID NO: 3; and
  (iv) such a molecule comprising in sequence the hypervariable regions $CDR1_i$, $CDR2_i$, and $CDR3_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Similarly, by the term "direct CDR-x equivalents thereof" are meant IL-17 binding molecules comprising in sequence the hypervariable regions $CDR1_i$-x, $CDR2_i$-x, and $CDR3_i$-x, (instead of CDR1-x, CDR2-x, and CDR3-x), wherein
  (v) the hypervariable region $CDR1_i$-x differs by 3, preferably 2, more preferably 1 amino acid(s) from the hypervariable region CDR1-x as shown in SEQ ID NO: 11; and
  (vi) the hypervariable region $CDR2_i$-x differs by 3, preferably 2, more preferably 1 amino acid(s) from the hypervariable region CDR2-x as shown in SEQ ID NO: 12; and
  (vii) the hypervariable region $CDR3_i$-x differs by 3, preferably 2, more preferably 1 amino acid(s) from the hypervariable region CDR3-x as shown in SEQ ID NO: 13; and
  (viii) such a molecule comprising in sequence the hypervariable regions $CDR1_i$-x, $CDR2_i$-x, and $CDR3_i$-x is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Similarly, by the term "direct CDR' equivalents thereof" is meant a domain comprising in sequence the hypervariable regions $CDR1'_i$, $CDR2'_i$, and $CDR3'_i$, wherein
  (i) the hypervariable region $CDR1'_i$ differs by 3, preferably 2, more preferably 1 amino acid(s) from the hypervariable region CDR1' as shown in SEQ ID NO: 4; and
  (ii) the hypervariable region $CDR2'_i$ differs by 3, preferably 2, more preferably 1 amino acid(s) from the hypervariable region CDR2' as shown in SEQ ID NO: 5; and
  (iii) the hypervariable region $CDR3'_i$ differs by 3, preferably 2, more preferably 1 amino acid(s) from the hypervariable region CDR3' as shown in SEQ ID NO: 6; and
  (iv) such a molecule comprising in sequence the hypervariable regions $CDR1'_i$, $CDR2'_i$, and $CDR3'_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Alternatively, an IL-17 binding molecule according to the invention may be an IL-17 binding molecule which comprises at least one antigen binding site comprising at least one immunoglobulin heavy chain variable domain ($V_H$) which comprises in sequence
  a) hypervariable regions CDR1 (SEQ ID NO: 1), CDR2 (SEQ ID NO: 2) and CDR3 (SEQ ID NO: 3); or
  b) hypervariable regions $CDR1_i$, $CDR2_i$, $CDR3_i$, said hypervariable region $CDR1_i$ differs by 3, preferably 2, more preferably 1 amino acid(s) from the hypervariable region of CDR1 as shown in SEQ ID NO: 1, said hypervariable region $CDR2_i$ differs by 3, preferably 2, more preferably 1 amino acid(s) from the hypervariable region of CDR2 as shown in SEQ ID NO: 2; and said hypervariable region $CDR3_i$ differs by 3, preferably 2, more preferably 1 amino acid(s) from the hypervariable region of CDR3 as shown in SEQ ID NO: 3; and
said binding IL-17 molecule comprising in sequence the hypervariable regions $CDR1_x$, $CDR2_x$, and $CDR3_x$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Similarly, an IL-17 binding molecule according to the invention may be an IL-17 binding molecule which comprises at least one antigen binding site comprising at least one immunoglobulin heavy chain variable domain ($V_H$) which comprises in sequence
  a) hypervariable regions CDR1-x (SEQ ID NO: 11), CDR2-x (SEQ ID NO: 12) and CDR3-x (SEQ ID NO: 13); or
  b) hypervariable regions $CDR1_i$-x, $CDR2_i$-x, $CDR3_i$-x, said hypervariable region $CDR1_i$-x differs by 3, preferably 2, more preferably 1 amino acid(s) from the hypervariable region of CDR1-x as shown in SEQ ID NO: 11, said hypervariable region $CDR2_i$-x differs by 3, preferably 2, more preferably 1 amino acid(s) from the hypervariable region of CDR2-x as shown in SEQ ID NO: 12; and said hypervariable region $CDR3_i$-x differs by 3, preferably 2, more preferably 1 amino acid(s) from the hypervariable region of CDR3-x as shown in SEQ ID NO: 13; and said binding IL-17 molecule comprising in sequence the hypervariable regions $CDR1_i$-x, $CDR2_i$-x, and $CDR3_i$-x is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Similarly, an IL-17 binding molecule according to the invention may be an IL-17 binding molecule which comprises at least one antigen binding site comprising at least one immunoglobulin light chain variable domain ($V_L$) which comprises in sequence
  a) hypervariable regions CDR'1 (SEQ ID NO: 4), CDR'2 (SEQ ID NO: 5) and CDR'3 (SEQ ID NO: 6); or
  b) hypervariable regions $CDR1'_i$, $CDR2'_i$, $CDR3'_i$, said hypervariable region $CDR'1_i$ differs by 3, preferably 2, more preferably 1 amino acid(s) from the hypervariable region of CDR'1 as shown in SEQ ID NO: 4, said hypervariable region $CDR'2_i$ differs by 3, preferably 2, more preferably 1 amino acid(s) from the hypervariable region of CDR'2 as shown in SEQ ID NO: 5; and said hypervariable region $CDR'3_i$ differs by 3, preferably 2, more preferably 1 amino acid(s) from the hypervariable region of CDR'3 as shown in SEQ ID NO: 6; and
said binding IL-17 molecule comprises in sequence the hypervariable regions $CDR'1_i$, $CDR'2_i$, and $CDR'3_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Alternatively, an IL-17 binding molecule according to the invention may be a IL-17 binding molecule comprising both heavy ($V_H$) and light chain ($V_L$) variable domains and said IL-17 binding molecule comprises at least one antigen binding site comprising:
a) an immunoglobulin heavy chain variable domain ($V_H$) which comprises in sequence hypervariable regions CDR1 (SEQ ID NO: 1), CDR2 (SEQ ID NO: 2) and CDR3 (SEQ ID NO: 3); and
an immunoglobulin light chain variable domain ($V_L$) which comprises in sequence hypervariable regions CDR1' (SEQ ID NO: 4), CDR2' (SEQ ID NO: 5) and CDR3' (SEQ ID NO: 6); or
b) an immunoglobulin heavy chain variable domain ($V_H$) which comprises in sequence hypervariable regions CDR1$_i$, CDR2$_i$, and CDR3$_i$, said hypervariable region hypervariable regions CDR1$_i$, CDR2$_i$, CDR3$_i$, said hypervariable region CDR1$_i$ differs by 3, preferably 2, more preferably 1 amino acid(s) from the hypervariable region of CDR1 as shown in SEQ ID NO: 1, said hypervariable region CDR2$_i$ differs by 3, preferably 2, more preferably 1 amino acid(s) from the hypervariable region of CDR2 as shown in SEQ ID NO: 2; and said hypervariable region CDR3$_i$ differs by 3, preferably 2, more preferably 1 amino acid(s) from the hypervariable region of CDR3 as shown in SEQ ID NO: 3; and
an immunoglobulin light chain variable domain ($V_L$) which comprises in sequence hypervariable regions CDR1'$_i$, CDR2'$_i$, CDR3'$_i$, said hypervariable region CDR'1$_i$ differs by 3, preferably 2, more preferably 1 amino acid(s) from the hypervariable region of CDR'1 as shown in SEQ ID NO: 4, said hypervariable region CDR'2$_i$ differs by 3, preferably 2, more preferably 1 amino acid(s) from the hypervariable region of CDR'2 as shown in SEQ ID NO: 5; and said hypervariable region CDR'3$_i$ differs by 3, preferably 2, more preferably 1 amino acid(s) from the hypervariable region of CDR'3 as shown in SEQ ID NO: 6; and
said binding IL-17 molecule defined in b) comprises in sequence the hypervariable regions CDR1$_i$, CDR2$_i$, CDR3$_i$, CDR'1$_i$, CDR'2$_i$, and CDR'3$_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

Alternatively, an IL-17 binding molecule according to the invention may be a IL-17 binding molecule comprising both heavy ($V_H$) and light chain ($V_L$) variable domains and said IL-17 binding molecule comprises at least one antigen binding site comprising:
a) an immunoglobulin heavy chain variable domain ($V_H$) which comprises in sequence hypervariable regions CDR1-x (SEQ ID NO: 11), CDR2-x (SEQ ID NO: 12) and CDR3-x (SEQ ID NO: 13); and
an immunoglobulin light chain variable domain ($V_L$) which comprises in sequence hypervariable regions CDR1' (SEQ ID NO: 4), CDR2' (SEQ ID NO: 5) and CDR3' (SEQ ID NO: 6); or
b) an immunoglobulin heavy chain variable domain ($V_H$) which comprises in sequence hypervariable regions CDR1$_i$-x, CDR2$_i$-x, and CDR3$_i$-x, said hypervariable region hypervariable regions CDR1$_i$-x, CDR2$_i$-x, CDR3$_i$-x, said hypervariable region CDR1$_i$-x differs by 3, preferably 2, more preferably 1 amino acid(s) from the hypervariable region of CDR1-x as shown in SEQ ID NO: 11, said hypervariable region CDR2$_i$-x differs by 3, preferably 2, more preferably 1 amino acid(s) from the hypervariable region of CDR2-x as shown in SEQ ID NO: 12; and said hypervariable region CDR3$_i$-x differs by 3, preferably 2, more preferably 1 amino acid(s) from the hypervariable region of CDR3-x as shown in SEQ ID NO: 13; and
an immunoglobulin light chain variable domain ($V_L$) which comprises in sequence hypervariable regions CDR1'$_i$, CDR2'$_i$, CDR3'$_i$, said hypervariable region CDR'1$_i$ differs by 3, preferably 2, more preferably 1 amino acid(s) from the hypervariable region of CDR'1 as shown in SEQ ID NO: 4, said hypervariable region CDR'2$_i$ differs by 3, preferably 2, more preferably 1 amino acid(s) from the hypervariable region of CDR'2 as shown in SEQ ID NO: 5; and said hypervariable region CDR'3$_i$ differs by 3, preferably 2, more preferably 1 amino acid(s) from the hypervariable region of CDR'3 as shown in SEQ ID NO: 6; and
said binding IL-17 molecule defined in b) comprises in sequence the hypervariable regions CDR1$_i$, CDR2$_i$, CDR3$_i$, CDR'1$_i$, CDR'2$_i$, and CDR'3$_i$ is capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts.

The inhibition of the binding of IL-17 to its receptor may be conveniently tested in various assays including such assays are described e.g. in PCT/EP2005/008470. By the term "to the same extent" is meant that the reference and the equivalent molecules exhibit, on a statistical basis, essentially identical IL-17 inhibitory activity in one of the assays referred to herein. For example, IL-17 binding molecules of the invention typically have $IC_{50}$s for the inhibition of human IL-17 on IL-6 production induced by human IL-17 in human dermal fibroblasts which are within +/−x5, i.e. below 10 nM, more preferably 9, 8, 7, 6, 5, 4, 3 or 2 nM of that of, preferably substantially the same as, the $IC_{50}$ of the corresponding reference molecule when assayed as described in Example 1 in PCT/EP2005/008470.

Alternatively, the assay used may be an assay of competitive inhibition of binding of IL-17 by soluble IL-17 receptors (e.g. the human IL-17 R/Fc constructs of Example 1) and the IL-17 binding molecules of the invention.

Most preferably, the human IL-17 antibody comprises at least
a) one heavy chain which comprises a variable domain having an amino acid sequence substantially identical to that shown in SEQ ID NO: 8 starting with the amino acid at position 1 and ending with the amino acid at position 127 and the constant part of a human heavy chain; and
b) one light chain which comprises a variable domain having an amino acid sequence substantially identical to that shown in SEQ ID NO: 10 starting with the amino acid at position 1 and ending with the amino acid at position 109 and the constant part of a human light chain.

The constant part of a human heavy chain may be of the $\gamma_1$, $\gamma_2$, $\gamma_3$, $\gamma_4$, $\mu$, $\alpha_1$, $\alpha_2$, $\delta$ or $\epsilon$ type, preferably of the $\gamma$ type, more preferably of the $\gamma_1$ type, whereas the constant part of a human light chain may be of the $\kappa$ or $\lambda$ type (which includes the $\lambda_1$, $\lambda_2$ and $\lambda_3$ subtypes) but is preferably of the $\kappa$ type. The amino acid sequences of all these constant parts are given in Kabat et al (supra).

Conjugates of the binding molecules of the invention, e.g. enzyme or toxin or radioisotope conjugates, are also included within the scope of the invention.

"Polypeptide", if not otherwise specified herein, includes any peptide or protein comprising amino acids joined to each other by peptide bonds, having an amino acid sequence starting at the N-terminal extremity and ending at the C-terminal extremity. Preferably the polypeptide of the present invention is a monoclonal antibody, more preferred is a chimeric (also called V-grafted) or humanised (also called CDR-grafted) monoclonal antibody, most preferred a fully human antibody obtainable e.g. by the technology exemplified in Example 1. The humanised (CDR-grafted) or fully human monoclonal antibody may or may not include further mutations introduced into the framework (FR) sequences of the acceptor antibody.

A functional derivative of a polypeptide as used herein includes a molecule having a qualitative biological activity in common with a polypeptide to the present invention, i.e. having the ability to bind to the human IL-17. A functional derivative includes fragments and peptide analogs of a polpypeptide according to the present invention. Fragments comprise regions within the sequence of a polypeptide according to the present invention, e.g. of a specified sequence. The term "derivative" is used to define amino acid sequence variants, and covalent modifications of a polypeptide according to the present invention. e.g. of a specified sequence. The functional derivatives of a polypeptide according to the present invention, e.g. of a specified sequence, e.g. of the hypervariable region of the light and the heavy chain, preferably have at least about 65%, more preferably at least about 75%, even more preferably at least about 85%, most preferably at least about 95, 96, 97, 98, 99% overall sequence homology with the amino acid sequence of a polypeptide according to the present invention, e.g. of a specified sequence, and substantially retain the ability to bind the human IL-17 or e.g. neutralize IL-6 production of IL-17 induced human dermal fibroblasts.

The term "covalent modification" includes modifications of a polypeptide according to the present invention, e.g. of a specified sequence; or a fragment thereof with an organic proteinaceous or non-proteinaceous derivatizing agent, fusions to heterologous polypeptide sequences, and post-translational modifications. Covalent modified polypeptides, e.g. of a specified sequence, still have the ability to bind the human IL-17 or e.g. neutralize IL-6 production of IL-17 induced human dermal fibroblasts by crosslinking. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains, see e.g. T. E. Creighton, Proteins: Structure and Molecular Properties, W. H. Freeman & Co., San Francisco, pp. 79-86 (1983). Covalent modifications e.g. include fusion proteins comprising a polypeptide according to the present invention, e.g. of a specified sequence and their amino acid sequence variants, such as immunoadhesins, and N-terminal fusions to heterologous signal sequences.

"Homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known.

"Amino acid(s)" refer to all naturally occurring L-α-amino acids, e.g. and including D-amino acids. The amino acids are identified by either the well known single-letter or three-letter designations.

The term "amino acid sequence variant" refers to molecules with some differences in their amino acid sequences as compared to a polypeptide according to the present invention, e.g. of a specified sequence. Amino acid sequence variants of a polypeptide according to the present invention, e.g. of a specified sequence, still have the ability to bind the human IL-17 or e.g. neutralize IL-6 production of IL-17 induced human dermal fibroblasts. Substitutional variants are those that have at least one amino acid residue removed and a different amino acid inserted in its place at the same position in a polypeptide according to the present invention, e.g. of a specified sequence. These substitutions may be single, where only one amino acid in the molecule has been substituted, or they may be multiple, where two or more amino acids have been substituted in the same molecule. Insertional variants are those with one or more amino acids inserted immediately adjacent to an amino acid at a particular position in a polypeptide according to the present invention, e.g. of a specified sequence. Immediately adjacent to an amino acid means connected to either the α-carboxy or α-amino functional group of the amino acid. Deletional variants are those with one or more amino acids in a polypeptide according to the present invention, e.g. of a specified sequence, removed. Ordinarily, deletional variants will have one or two amino acids deleted in a particular region of the molecule.

The desired antibody may be produced in a cell culture or in a transgenic animal. A suitable transgenic animal may be obtained according to standard methods which include micro injecting into eggs the first and second DNA constructs placed under suitable control sequences transferring the so prepared eggs into appropriate pseudo-pregnant females and selecting a descendant expressing the desired antibody.

When the antibody chains are produced in a cell culture, the DNA constructs must first be inserted into either a single expression vector or into two separate but compatible expression vectors, the latter possibility being preferred.

Accordingly, the invention also provides an expression vector able to replicate in a prokaryotic or eukaryotic cell line which comprises at least one of the DNA constructs above described.

Each expression vector containing a DNA construct is then transferred into a suitable host organism. When the DNA constructs are separately inserted on two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin, e.g. a myeloma, hybridoma or a normal immortalised B-cell, which conveniently does not express any endogenous antibody heavy or light chain.

For expression in mammalian cells it is preferred that the IL-17 binding molecule coding sequence is integrated into the host cell DNA within a locus which permits or favours high level expression of the IL-17 binding molecule. Cells in which the IL-17 binding molecule coding sequence is integrated into such favourable loci may be identified and selected on the basis of the levels of the IL-17 binding molecule which they express. Any suitable selectable marker may be used for preparation of host cells containing the IL-17 binding molecule coding sequence; for instance, a dhfr gene/methotrexate or equivalent selection system may be used. Alternative systems for expression of the IL-17 binding molecules of the invention include GS-based amplification/selection systems, such as those described in EP 0256055 B, EP 0323997 B and European patent application 89303964.4.

For the purposes of the present description an antibody is "capable of inhibiting the binding of IL-17 as AIN457" if the antibody is capable of inhibiting the binding of IL-17 to its receptor substantially to the same extent as the AIN457 antibody, wherein "to the same extent" has meaning as defined above.

The AIN457 antibody has binding affinity for IL-17 which is higher than affinities previously reported for anti-IL-17 antibodies, in particular to any anti human IL-17 antibodies. Thus AIN457 has a dissociation equilibrium constant $K_D$ for binding to IL-17 of about 0.188±0.036 nM (determined by BIAcore, e.g. as described in PCT application PCT/EP2005/008470). This high binding affinity makes the AIN457 antibody particularly suitable for therapeutic applications.

In the present description the terms "treatment" or "treat" refer to both prophylactic or preventative treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse.

IL-17 binding molecules as defined above which have binding specificity for human. IL-17, in particular antibodies which are capable of inhibiting the binding of IL-17 to its receptor; and antibodies to IL-17 which are capable of inhibiting the activity of 1 nM (=30 ng/ml) human IL-17 at a concentration of 50 nM, preferably 20 nM, more preferably 10 nM, more preferably 5 nM of said molecule by 50%, said inhibitory activity is measured on IL-6 production induced by hu-IL-17 in human dermal fibroblasts, are herein referred to as Antibodies of the Invention.

Preferably the Antibodies of the Invention are human antibodies, most preferably the AIN457 antibody or direct equivalents thereof.

Pharmacological activities of the Antibodies of the Invention may be demonstrated in standard test methods for example as described below:

Neutralization of IL-17 dependent production of interleukin-6 by primary human fibroblasts: The production of IL-6 in primary human (dermal) fibroblasts is dependent on IL-17 (Hwang S Y et al., (2004) Arthritis Res Ther; 6:R120-128.

In short, human dermal fibroblasts are stimulated with recombinant IL-17 in the presence of various concentrations of Antibody of the Invention or human IL-17 receptor with Fc part. The chimeric anti-CD25 antibody Simulect® (basiliximab) is used as a negative control. Supernatant is taken after 16 h stimulation and assayed for IL-6 by ELISA. Antibodies of the Invention typically have $IC_{50}$s for inhibition of IL-6 production (in the presence 1 nM human IL-17) of about 50 nM or less (e.g. from about 0.01 to about 50 nM) when tested as above, i.e. said inhibitory activity is measured on IL-6 production induced by hu-IL-17 in human dermal fibroblasts. Preferably, the Antibodies of the Invention have an $IC_{50}$ for inhibition of IL-6 production as defined above of about 20 nM or less, more preferably of about 10 nM or less, more preferably of about 5 nM or less, more preferably of about 2 nM or less, more preferably of about 1 nM or less.

As indicated in the above assay Antibodies of the Invention potently block the effects of IL-17. Accordingly, the Antibodies of the Invention have pharmaceutical utility as follows:

Antibodies of the Invention are useful for the prophylaxis and treatment of IL-17 mediated diseases or medical conditions, e.g. inhibiting the growth of solid or hematological malignant proliferative diseases.

Solid malignant diseases may include malignant tumor diseases wherever the tumor (or the metastasis) are located. Preferably the malignant tumor disease is breast cancer, genitourinary cancer, lung cancer, gastrointestinal cancer e.g. colorectal tumor or genitourinary tumor, especially a prostate cancer or a gastrointestinal stromal tumor (GIST), epidermoid cancer, melanoma, ovarian cancer, pancreas cancer, neuroblastoma, head and neck cancer such as e.g. mouth cancer or laryngeal cancer, bladder cancer, or in a broader sense renal, brain or gastric cancer, a lung tumor, especially a non-small cell lung tumor.

Hematological malignant diseases ("liquid tumors") include for instance lymphoma, leukemia, especially those expressing c-kit, KDR, Flt-1 or Flt-3, myeloma or lymphoid malignancies, but also cancers of the spleen and cancers of the lymph nodes. More particular examples of such B-cell associated cancers, including for example, high, intermediate and low grade lymphomas (including B cell lymphomas such as, for example, mucosa-associated-lymphoid tissue B cell lymphoma and non-Hodgkin's lymphoma, mycosis fungoides, Sezary Syndrome, mantle cell lymphoma, Burkitt's lymphoma, small lymphocytic lymphoma, marginal zone lymphoma, diffuse large cell lymphoma, follicular lymphoma, and Hodgkin's lymphoma and T cell lymphomas) and leukemias (including secondary leukemia, chronic lymphocytic leukemia, such as B cell leukemia (CD5+ B lymphocytes), myeloid leukemia, such as acute myeloid leukemia, chronic myeloid leukemia, lymphoid leukemia, such as acute lymphoblastic leukemia and myelodysplasia), multiple myeloma, such as plasma cell malignancy, and other hematological and/or B cell- or T-cell-associated cancers. Also included are cancers of additional hematopoietic cells, including polymorphonuclear leukocytes, such as basophils, eosinophils, neutrophils and monocytes, dendritic cells, platelets, erythrocytes and natural killer cells. The origins of B-cell cancers are as follows: marginal zone B-cell lymphoma origins in memory B-cells in marginal zone, follicular lymphoma and diffuse large B-cell lymphoma originates in centrocytes in the light zone of germinal centers, multiple myeloma originates in plasma cells, chronic lymphocytic leukemia and small lymphocytic leukemia originates in B1 cells (CD5+), mantle cell lymphoma originates in naive B-cells in the mantle zone and Burkitt's lymphoma originates in centroblasts in the dark zone of germinal centers.

For these indications, the appropriate dosage will, of course, vary depending upon, for example, the particular Antibody of the Invention to be employed, the host, the mode of administration and the nature and severity of the condition being treated. However, in prophylactic use, satisfactory results are generally indicated to be obtained at dosages from about 0.05 mg to about 20 mg or 10 mg per kilogram body weight more usually from about 0.1 mg to about 5 mg per kilogram body weight. The frequency of dosing for prophylactic uses will normally be in the range from about once per week up to about once every 3 months, more usually in the range from about once every 2 weeks up to about once every 10 weeks, e.g. once every 4 to 8 weeks. Antibody of the Invention is conveniently administered parenterally, intravenously, e.g. into the antecubital or other peripheral vein, intramuscularly, or subcutaneously. A prophylactic treatment typically comprises administering the Antibody of the Invention once per month to once every 2 to 3 months, or less frequently.

The Antibodies of the Invention may be administered as the sole active ingredient or in conjunction with, e.g. as an adjuvant to or in combination to, other drugs e.g. drugs useful in the treatment, prevention, amelioration and/or cure of cancers, e.g. for the treatment or prevention of diseases mentioned above. For example, the Antibodies of the Invention may be used in combination with a chemotherapeutic agent. Chemotherapeutic agents that may be administered with the antibodies of the invention include, but are not limited to, antibiotic derivatives (e.g., doxorubicin (adriamycin), bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, etoposide, Topotecan, 5-Fluorouracil, paclitaxel (Taxol), Cisplatin, Cytarabine, and IFN-gamma, irinotecan (Camptosar, CPT-11), irinotecan analogs, gemcitabine (GEMZAR®), and oxaliplatin, ifosamide, and nitosourea compounds).

In specific embodiments, antibodies of the present invention may be administered in combination with one or more chemotherapeutic or other therapeutic agents useful in the treatment, prevention, amelioration and/or cure of cancers including, but not limited to, one or more agents of TABLE 1. Table 1:

81C6 (Anti-tenascin monoclonal antibody), 2-chlorodeoxyadenosine, A007 (4-4'-dihydroxybenzophenone-2,4-dinitrophenyihydrazone), Abarelix® (Abarelix-Depot-M®, PPI-149, R-3827); Abiraterone Acetate® (CB-7598, CB-7630), ABT-627 (ET-1 inhibitor), ABX-EGF (anti-EGFr MAb), Acetyldinaline (CI-994, GOE-5549, GOR-5549, PD-130636), AG-2034 (AG-2024, AG-2032, GARFT [glycinamide ribonucleoside transformylase] inhibitor), Alanosine, Aldesleukin (IL-2, Proleukin®), Alemtuuumab® (Campath®), Alitretinoin (Panreting, LGN-1057), Allopurinol (Aloprim®, Zyloprim®), Altretamine (Hexalen®, hexamethylmelamine, Hexastat®), Amifostine (Ethyol®), Aminocamptothecin (9-AC, 9-Aminocamptothecin, NSC 603071), Aminoglutethimide (Cytadren®), Aminolevulinic acid (Levulan®, Kerastick®), Aminopterin, Amsacrine, Anastrozole (Arimidex®), Angiostatin, Annamycin (AR-522, annamycin LF, Aronex®), Anti-idiotype therapy (BsAb), Anti-CD19/CD3 MAb (anti-CD19/CD3 scFv, anti-NHL MAb), APC-8015 (Provenge®, Dendritic cell therapy), Aplidine (Aplidin®, Aplidina®), Arabinosylguanine (Ara-G, GW506U78, Nelzarabine®, Compound 506U78), Arsenic trioxide (Trisenox®, ATO, Atrivex®), Avorelin® (Meterelin®, MF-6001, EP-23904), B43-Genistein (anti-CD19 Ab/genistein conjugate), B43-PAP (anti-CD19 Ab/pokeweed antiviral protein conjugate), B7 antibody conjugates, BAY 43-9006 (Raf kinase inhibitor), BBR 3464, Betathine (Beta-LT), Avastin® (Bevacizumab, Anti-VEGF monoclonal antibody, rhuMAb-VEGF), Sutent® (sunitinib malate), Nexavar® (sorafenib tosylate), RAD001 (everolimus), Bexarotene (Targretin®, LGD1069), BIBH-1 (Anti-FAP MAb), BIBX-1382, Biclutamide (Casodex®), Biricodar dicitrate (Incel®, Incel MDR Inhibitor), Bleomycin (Blenoxane®), BLP-25 (MUC-1 peptide), BLyS antagonists, BMS-214662 (BMS-192331, BMS-193269, BMS-206635), BNP-1350 (BNPI-1100, Karenitecins), Boronated Protoporphyrin Compound (PDIT, Photodynamic Immunotherapy), Bryostatin-1 (Bryostatin®, BMY-45618, NSC-339555), Budesonide (Rhinocort®), Busulfan (Busulfex®, Myleran®), C225 (IMC-225, EGFR inhibitor, Anti-EGFr MAb, Erbitux® (Cetuximab), C242-DM1 (huC242-DM1), Cabergoline (Dostinex®), Capecitabine (Xeloda®, Doxifluridine®, oral 5-FU), Carbendazin® (FB-642), Carboplatin (Paraplatin®, CBDCA), Carboxyamidotriazole (NSC 609974, CAI, L-651582), Carmustine (DTI-015, BCNU, BiCNU, Gliadel Wafer®), CC49-zeta gene therapy, CEA-cide®) (Labetuzumab®, Anti-CEA monoclonal antibody, hMN-14), CeaVac® (MAb 3H1), Celecoxib (Celebrex®), CEP-701 (KT-5555), Cereport® (Lobradimil®, RMP-7), Chlorambucil (Leukeran®), CHML (Cytotropic Heterogeneous Molecular Lipids), Cholecaliferol, CI-1033 (Pan-erbB RTK inhibitor), Cilengitide (EMD-121974, integrin alphavbeta3 antagonist), Cisplatin (Platinol®, CDDP), Cisplatin-epinephrine gel (IntraDose®, FocaCist®), Cisplatin-liposomal (SP1-077), 9-cis retinoic acid (9-cRA), Cladribine (2-CdA, Leustatin®), Clofarabine (chloro-fluoro-araA), Clonadine hydrochloride (Duraclon®), CMB-401 (Anti-PEM MAb/calicheamycin), CMT-3 (COL-3, Metastat®), Cordycepin, Cotara® (chTNT-1/B, [1311]-chTNT-1/B), CN-706, CP-358774 (Tarceva®, OSI-774, EGFR inhibitor), CP-609754, CP IL-4-toxin (IL-4 fusion toxin), CS-682, CT-2584 (Apra®, CT-2583, CT-2586, CT-3536), CTP-37 (Avicine®, hCG blocking vaccine), Cyclophosphamide (Cytoxan®, Neosar®, CTX), Cytarabine (Cytosar-U®, ara-C, cytosine arabinoside, DepoCyt®, D-limonene, DAB389-EGF (EGF fusion toxin), Dacarbazine (DTIC), Daclizumab® (Zenapax®), Dactinomycin (Cosmegen®), Daunomycin (Daunorubicin®, Cerubidine®), Daunorubicin (DaunoXome®, Daunorubicin®, Cerubidine®), DeaVac® (CEA anti-idiotype vaccine), Decitabine (5-aza-2'-deoxyytidine), Declopramide (Oxi-104), Denileukin diftitox (Ontak®), Depsipeptide (FR901228, FK228), Dexamethasone (Decadron®), Dexrazoxane (Zinecard®), Diethylnorspermine (DENSPM), Diethylstilbestrol (DES), Dihydro-5-azacytidine, Docetaxel (Taxotere®, Taxane®), Dolasetron mesylate (Anzemet®), Dolastatin-10 (DOLA-10, NSC-376128), Doxorubicin (Adriamycin®, Doxil®, Rubex®), DPPE, DX-8951f (DX-8951), Edatrexate, EGF-P64k Vaccine, Elliott's B Solution®, EMD-121974, Endostatin, Eniluracil (776c85), E09 (E01, E04, E068, E070, E072), Epirubicin (Ellence®, EPI, 4' epi-doxorubicin), Epratuzumab® (Lymphocide®, humanized anti-CD22, HAT), Erythropoietin (EPO®, Epogen®, Procrit®), Estramustine (Emcyt®), Etanidazole (Radinyl®), Etoposide phosphate (Etopophos®), Etoposide (VP-16, Vepesid®), Exemestane (Aromasin®, Nikidess®), Exetecan mesylate (DX-8951, DX-8951f), Exisulind (SAAND, Aptosyn®, cGMP-PDE2 and 5 inhibitor), F19 (Anti-FAP monoclonal antibody, iodinated anti-FAP MAb), Fadrozole (Afema®, Fadrozole hydrochloride, Arensin®), Fenretinide® (4HPR), Fentanyl citrate (Actiq®), Filgrastim (Neupogen®, G-CSF), FK-317 (FR-157471, FR-70496), Flavopiridol (HMR-1275), Fly3/flk2 ligand (Mobista®), Fluasterone, Fludarabine (Fludara®, FAMP), Fludeoxyglucose (F-18®), Fluorouracil (5-FU, Adrucil®, Fluoroplex®, Efudex®), Flutamide (Eulexin®), FMdC (KW-2331, MDL-101731), Formestane (Lentaron®), Fotemustine (Nuphoran®, Mustophoran®), FUDR (Floxuridine®), Fulvestrant (Faslodex®), G3139 (Genasense®, GentaAnticode®, Bcl-2 antisense), Gadolinium texaphyrin (Motexafin gadolinium, Gd-Tex®, Xcytrin®), Galarubicin hydrochloride (DA-125), GBC-590, Gastrimmune® (Anti-gastrin-17 immunogen, anti-g17), Gemcitabine (Gemto®, Gemzar®), Gentuzumab-ozogamicin (Mylotarg®), GL331, Globo H hexasaccharide (Globo H-KLH®), Glufosfamideg (β-D-glucosyl-isofosfamide mustard, D19575, INN), Goserelin acetate (Zoladex®), Granisetron (Kytril®), GVAX (GM-CSF gene therapy), Her-2/Neu vaccine, Herceptin® (Trastuzumab®, Anti-HER-2 monoclonal antibody, Anti-EGFR-2 MAb), HSPPC-96 (HSP cancer vaccine, gp96 heat shock protein-peptide complex), Hu1D10 (anti-HLA-DR MAb, SMART 1D10), HumaLYM (anti-CD₂O MAb), Hydrocortisone, Hydroxyurea (Hydrea®), Hypericin® (VltRxyn®), 1-131 Lipidiol®, Ibritumomab®tiuxetan (Zevalin®), Idarubicin (Idamycin®, DMDR, IDA), Ifosfamide (IFEX®), Imatinib mesylate (STI-571, Imatinib®, Glivec®, Gleevec®, Ab1 tyrosine kinase inhibitor), INGN-101 (p53 gene therapy/retrovirus), INGN-201 (p53 gene therapy/adenovirus), Interferon alpha (Alfaferone®, Alpha-IF®), Interferon alpha 2a (Intron A®), Interferon gamma (Gamma-interferon, Gamma 100®, Gamma-IF), Interleukin-2 (ProleiukinR®), Intoplicine (RP 60475), Irinotecan (Camptosar®, CPT-11, Topotecin®, CaptoCPT-1), Irofulven (MG1-114, Ivofulvan, Acylfulvene analogue), ISIS-2053 (PKC-alpha antisense), ISIS-2503 (Ras antisense), ISIS-3521 (PKC-alpha antisense), ISIS-5132 (K-ras/raf antisense), Isotretinoin (13-CRA, 13-cis retinoic acid, Accutane®), Ketoconazole (Nizoral®), KRN-8602 (MX, MY-5, NSC-619003, MX-2), L-778123 (Ras inhibitors), L-asparaginase (Elspar®, Crastinin®, Asparaginase Medac®, Kidrolase®), Leflunomide (SU-101, SU-0200), Letrozole (Femara®), Leucovorin (Leucovorin®, Wellcovorin®), Leuprolide acetate (Viadur®, Lupron®, Leuprogel®, Eligard®), Leuvectin® (cytofectin+IL-2 gene, IL-2 gene therapy), Levamisole (Ergamisol®), Liarozole (Liazal, Liazol, R-75251, R-85246, Ro-85264), Lmb-2 immunotoxin (anti-CD25 recombinant immuno toxin, anti-Tac (Fv)-PE38), Lometrexol (T-64, T-904064), Lomustine (CCNU®, CeeNU®), LY-335979, Lym-1 (131-I LYM-1), Lymphoma vaccine (Genitope), Mannan-MUC1 vaccine, Marimastat® (BB-2516, TA-2516, MMP inhibitor), MDX-447 (MDX-220, BAB-447, EMD-82633, H-447, anti-EGFr/FcGammaR1r), Mechlorethamine (Nitrogen Mustard, HN2, Mustargen®), Megestrol acetate (Megace®, Pallace®), Melphalan (L-PAM, Alkeran®, Phenylalanine mustard), Mercaptopurine (6-mercaptopurine, 6-MP), Mesna (Mesnex®), Methotrexate® (MTX, Mexate®, Folex®), Methoxsalen (Uvadex®), 2-Methoxyestradiol (2-ME, 2-ME2), Methylprednisolone (Solumedrol®), Methyltestosterone (Android-100, Testred®, Virilon®), MGV, Mitomycin C (Mitomycin®, Mutamycin®, Mito Extra®), Mitoxantrone (Novantrone®, DHAD), Mitumomab® (BEC-2, EMD-60205), Mivobulin isethionate (CI-980), MN-14 (Anti-CEA immunoradiotherapy, 131I-MN-14, 188Re-MN-14), Motexafin Lutetium (Lutrin®, Optrin®, Lu-Tex®, lutetium texaphyrin, Lucyn®, Antrin®), MPV-2213ad (Finrozole®), MS-209, Muc-1 vaccine, NaPro Paclitaxel, Nelarabine (Compound 506, U78), Neovastat® (AE-941, MMP inhibitor), Neugene compounds (Oncomyc-NG, Resten-NG, myc antisense), Nilutamide (Nilandron®), NovoMAb-G2 scFv (NovoMAb-G2 IgM), O6-benzylguanine (BG, Procept®), Octreotide acetate (Sandostatin LAR® Depot), Odansetron (Zofran®), Onconase (Ranpirnase®), OncoVAX-CL, Onco-VAX-CL Jenner (GA-733-2 vaccine), OncoVAX-P (Onco-VAX-PrPSA), Onyx-015 (p53 gene therapy), Oprelvekin (Neumage®), Orzel (Tegafur+Uracil+Leucovorin), Oxaliplatin (Eloxatine®, Eloxatin®), Pacis® (BCG, live), Paclitaxel (Paxene®, Taxol®), Paclitaxel-DHA (Taxoprexin®), Pamidronate (Aredia®), PC SPES, Pegademase (Adagen®, Pegademase bovine), Pegaspargase® (Oncospar®), Peldesine (BCX-34, PNP inhibitor), Pemetrexed disodium (Alimta®, MTA, multitargeted antifolate, LY 231514), Pentostatin (Nipent®, 2-deoxycoformycin), Perfosfamide (4-hydroperoxycyclophosphamide, 4-HC), Perillyl alcohol (perilla alcohol, perillic alcohol, perillol, NSC-641066), Phenylbutyrate, Pirarubicin (THP), Pivaloyloxymethyl butyrate (AN-9, Pivanex®), Porfimer sodium (Photofrin®), Prednisone, Prinomastat® (AG-3340, MMP inhibitor), Procarbazine (Matulane®), PROSTVAC, Providence Portland Medical Center Breast Cancer Vaccine, PS-341 (LDP-341, 26S proteasome inhibitor), PSMA MAb (Prostate Specific Membrane Antigen monoclonal antibody), Pyrazoloacridine (NSC-366140, PD-115934), Quinine, R115777 (Zarnestra®), Raloxifene hydrochloride (Evista®, Keoxifene hydrochloride), Raltitrexed (Tomudex®, ZD-1694), Rebeccamycin, Retinoic acid, R-flurbiprofen (Flurizan, E-7869, MPC-7869), RFS-2000 (9-nitrocamptothecan, 9-NC, Rubitecan®), Rituximab® (Rituxan®, anti-CD20 MAb), RSR-13 (GSJ-61), Satraplatin (BMS-182751, JM-216), SCH-6636, SCH-66336, Sizofilan® (SPG, Sizofuran®, Schizophyllan®, Sonifilan®), SKI-2053R (NSC-D644591), Sobuzoxane (MST-16, Perazolin®), Squalamine (MSI-1256F), SR-49059 (vasopressin receptor inhibitor, V1a), Streptozocin (Zanosar®), SU5416 (Semaxanib®, VEGF inhibitor), SU6668 (PDGF-TK inhibitor), T-67 (T-138067, T-607), Talc (Sclerosol®), Tamoxifen (Nolvadex®), Taurolidine (Taurolin®), Temozolamide (Temodar®, NSC 362856), Teniposide (VM-26, Vumon®), TER-286, Testosterone (Andro®, Androderm®, Testoderm TTS®, Testoderm®, DepoTestosterone®, Androgel®, depoAndro®), Tf-CRM107 (Transferrin-CRM-107), Thalidomide, Theratope, Thioguanine (6-thioguanine, 6-TG), Thiotepa (triethylenethiophosphaoramide, Thioplex®), Thymosin alpha I (Zadaxin®, Thymalfasin®), Tiazofurin (Tiazole®), Tirapazamine (SR-259075, SR-4233, Tirazone®, Win-59075), TNP-470 (AGM-1470, Fumagillin), Tocladesine (8-Cl-cAMP), Topotecan (Hycamtin®, SK&F-104864, NSC-609699, Evotopin®), Toremifene (Estrirnex®, Fareston®), Tositumomab® (Bexxar®), Tretinoin (Retin-A®, Atragen®, ATRA, Vesanoid®), TriAb® (anti-idiotype antibody immune stimulator), Trilostane (Modrefen®), Triptorelin pamoate (Trelstar Depot®, Decapeptyl®), Trimetrexate (Neutrexin®), Troxacitabine (BCH-204, BCH-4556, Troxatyl®), TS-1, UCN-01 (7-hydroxystaurosporine), Valrubicin (Valstar®), Valspodar (PSC 833), Vapreotide® (BMY-41606), Vaxid (B-cell lymphoma DNA vaccine), Vinblastine (Velban®, VLB), Vincristine (Oncovin®, Onco TCS®, VCR, Leurocristine®), Vindesine (Eldisine®, Fildesin®), Vinflunine (Javlor®, tubulin polymerization inhibitor), Vinorelbine (Navelbine®), Vitaxin® (LM-609, integrin alphavbeta3 antagonistic MAb), WF10 (macrophage regulator), WHI-P131, WT1 Vaccine, XR-5000 (DACA), XR-9576 (XR-9351, P-glycoprotein/MDR inhibitor), ZD-9331, ZD-1839 (IRESSA®), and Zoledronate (Zometa®).

Preferred combination partner include Erbitux® (Cetuximab), Avastin® (Bevacizumab), Nexavar® (sorafenib tosylate), Sutent® (sunitinib malate), Tarceva® (erlotinib), RAD001 (everolimus), Docetaxel (Taxotere®), Cisplatin, Capecitabine (Xeloda®, Doxifluridine®, oral 5-FU).

In one embodiment, the present invention provides pharmaceutical composition comprising an Antibody of the Invention, in particular AIN457, as active ingredients and at least one further anti-cancer agent from TABLE 1, in which the active ingredients are present in each case in free form or in the form of a pharmaceutically acceptable salt and optionally at least one pharmaceutically acceptable carrier; for simultaneous, separate or sequential use. 1 In a preferred embodiment, the Antibody of the Invention, in particular AIN457, and the at least one further anti-cancer agent from TABLE 1 are comprised in a single pharmaceutical formulation. Such combination are, in accordance with the present invention, particularly useful for the treatment of a proliferative disease, such as cancer and in particular of solid malignant diseases or hematological malignant diseases.

In accordance with the foregoing the present invention provides in a yet further aspect:

A method as defined above comprising co-administration, e.g. concomitantly or in sequence, of a therapeutically effective amount of an IL-17 binding molecule, e.g. an Antibody of the Invention, and at least one second drug substance, said second drug substance being a immuno-suppressive/immunomodulatory, anti-inflammatory chemotherapeutic or anti-infectious drug, e.g. as indicated above.

Or, a therapeutic combination, e.g. a kit, comprising of a therapeutically effective amount of a) an IL-17 binding molecule, e.g. an Antibody of the Invention, and b) at least one second substance selected from a immuno-suppressive/immunomodulatory, anti-inflammatory chemotherapeutic or anti-infectious drug, e.g. as indicated above. The kit may comprise instructions for its administration.

Where the Antibodies of the Invention are administered in conjunction with other immuno-suppressive/immunomodulatory, anti-inflammatory chemotherapeutic or anti-infectious therapy, dosages of the co-administered combination compound will of course vary depending on the type of co-drug employed, e.g. whether it is a DMARD, anti-TNF, IL-1 blocker or others, on the specific drug employed, on the condition being treated and so forth.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinised blood into the saline at the time of formulation. Alternatively, the formulation is given subcutaneous. The presence of an excess of such physiologically inert protein prevents loss of antibody by adsorption onto the walls of the container and tubing used with the infusion solution. If albumin is used, a suitable concentration is from 0.5 to 4.5% by weight of the saline solution. Other formulations comprise liquid or lyophilized formulation.

The invention is further described by way of illustration in the following Examples.

EXAMPLES

Example 1

AIN457 antibody is generated and shown to bind with very high affinity to recombinant human IL-17 (huIL-17); the KD is 0.188±0.036 nM (BIAcore) and neutralizes human IL-6 production induced by huIL-17 in human dermal fibroblast; IC50 is 2.1±0.1 nM at a concentration of 1.87 nM huIL-17 as described in PCT application PCT/EP2005/008470.

Example 2

TABLE 2

Nucleotide and amino-acid sequence of the light chain

```
MV417   ACCATGGAAACCCCAGCGGAGCTTCTCTTCCTCCTGCTACTCTGGCTCCCAGATACCACC
      1 ---------+---------+---------+---------+---------+---------+  160
        TGGTACCTTTGGGGTCGCCTCGAAGAGAAGGAGGACGATGAGACCGAGGGTCTATGGTGG
        T  M  E  T  P  A  E  L  L  F  L  L  L  L  W  L  P  D  T  T   —

MV419   GGAGAAATTGTGTTGACGCAGTCTCCAGGCACCCTGTCTTTGTCTCCAGGGGAAAGAGCC
     61 ---------+---------+---------+---------+---------+---------+  120
        CCTCTTTAACACAACTGCGTCAGAGGTCCGTGGGACAGAAACAGAGGTCCCCTTTCTCGG
        G  E  I  V  L  T  Q  S  P  G  T  L  S  L  S  P  G  E  R  A   —

ACCCTCTCCTGCAGGGCCAGTCAGAGTGTTAGCAGCAGCTACTTAGCCTGGTACCAGCAG
    121 ---------+---------+---------+---------+---------+---------+  180
        TGGGAGAGGACGTCCCGGTCAGTCTCACAATCGTCGTCGATGAATCGGACCATGGTCGTC
        T  L  S  C  R  A  S  Q  S  V  S  S  S  Y  L  A  W  Y  Q  Q   —

AAACCTGGCCAGGCTCCCAGGCTCCTCATCTATGGTGCATCCAGCAGGGCCACTGGCATC
    181 ---------+---------+---------+---------+---------+---------+  240
        TTTGGACCGGTCCGAGGGTCCGAGGAGTAGATACCACGTAGGTCGTCCCGGTGACCGTAG
        K  P  G  Q  A  P  R  L  L  I  Y  G  A  S  S  R  A  T  G  I   —

CCAGACAGGTTCAGTGGCAGTGGGTCTGGGACAGACTTCACTCTCACCATCAGCAGACTG
    241 ---------+---------+---------+---------+---------+---------+  300
        GGTCTGTCCAAGTCACCGTCACCCAGACCCTGTCTGAAGTGAGAGTGGTAGTCGTCTGAC
        P  D  R  F  S  G  S  G  S  G  T  D  Y  T  L  T  I  S  R  L   —

GAGCCTGAAGATTTTGCAGTGTATTACTGTCAGCAGTATGGTAGCTCACCGTGCACCTTC
    301 ---------+---------+---------+---------+---------+---------+  360
        CTCGGACTTCTAAAACGTCACATAATGACAGTCGTCATACCATCGAGTGGCACGTGGAAG
        E  P  E  D  F  A  V  Y  Y  C  Q  Q  Y  G  S  S  P  C  T  F   —

GGCCAAGGGACACGACTGGAGATTAAACGAACTGTGGCTGCACCATCTGTCTTCATCTTC
    361 ---------+---------+---------+---------+---------+---------+  420
        CCGGTTCCCTGTGCTGACCTCTAATTTGCTTGACACCGACGTGGTAGACAGAAGTAGAAG
        G  Q  G  T  R  L  E  I  K  R  T  V  A  A  P  S  V  F  I  F   —
```

TABLE 2-continued

Nucleotide and amino-acid sequence of the light chain

```
        CCGCCATCTGATGAGCAGTTGAAATCTGGAACTGCCTCTGTTGTGTGCCTGCTGAATAAC
    421 ---------+---------+---------+---------+---------+---------+  480
        GGCGGTAGACTACTCGTCAACTTTAGACCTTGACGGAGACAACACACGGACGACTTATTG
         P  P  S  D  E  Q  L  K  S  G  T  A  S  V  V  C  L  L  N  N   -

TTCTATCCCAGAGAGGCCAAAGTACAGTGGAAGGTGGATAACGCCCTCCAATCGGGTAAC
    481 ---------+---------+---------+---------+---------+---------+  540
        AAGATAGGGTCTCTCCGGTTTCATGTCACCTTCCACCTATTGCGGGAGGTTAGCCCATTG
         F  Y  P  R  E  A  K  V  Q  W  K  V  D  N  A  L  Q  S  G  N   -

TCCCAGGAGAGTGTCACAGAGCAGGACAGCAAGGACAGCACCTACAGCCTCAGCAGCACC
    541 ---------+---------+---------+---------+---------+---------+  600
        AGGGTCCTCTCACAGTGTCTCGTCCTGTCGTTCCTGTCGTGGATGTCGGAGTCGTCGTGG
         S  Q  E  S  V  T  E  Q  D  S  K  D  S  T  Y  S  L  S  S  T   -

CTGACGCTGAGCAAAGCAGACTACGAGAAACACAAAGTCTACGCCTGCGAAGTCACCCAT
    601 ---------+---------+---------+---------+---------+---------+  660
        GACTGCGACTCGTTTCGTCTGATGCTCTTTGTGTTTCAGATGCGGACGCTTCAGTGGGTA
         L  T  L  S  K  A  D  Y  E  K  H  K  V  Y  A  C  E  V  T  H   -

CAGGGCCTGAGCTCGCCCGTCACAAAGAGCTTCAACAGGGGAGAGTGTTAG
    661 ---------+---------+---------+---------+---------+-  711
#223    GTCCCGGACTCGAGCGGGCAGTGTTTCTCGAAGTTGTCCCCTCTCACAATC
         Q  G  L  S  S  P  V  T  K  S  F  N  R  G  E  C  *   -
```

The amino-acid sequence coding for the variable domain is bold and underlined. The oligonucleotideprimers used for cloning are indicated (underlined).

TABLE 3

Nucleotide and amino-acid sequence of the heavy chain

```
MV416   ACCATGGAATTGGGGCTGAGCTGGGTTTTCCTTGTTGCTATTTTAGAAGGTGTCCACTGT
      1 ---------+---------+---------+---------+---------+---------+  60
        TGGTACCTTAACCCCGACTCGACCCAAAAGGAACAACGATAAAATCTTCCACAGGTGACA
         T  M  E  L  G  L  S  W  V  F  L  V  A  I  L  E  G  V  H  C   -

MV418   GAGGTGCAGTTGGTGGAGTCTGGGGGAGGCTTGGTCCAGCCIGGGGGGTCCCTGAGACTC
     61 ---------+---------+---------+---------+---------+---------+  120
        CTCCACGTCAACCACCTCAGACCCCCTCCGAACCAGGTCGGACCCCCCAGGGACTCTGAG
         E  V  Q  L  V  E  S  G  G  G  L  V  Q  P  G  G  S  L  R  L   -

TCCTGTGCAGCCTCIVGATTCACCTTTAGTAACTATTGGATGAACTGGGTCCGCCAGGCT
    121 ---------+---------+---------+---------+---------+---------+  180
        AGGACACGTCGGAGACCTAAGTGGAAATCATTGATAACCTACTTGACCCAGGCGGTCCGA
         S  C  A  A  S  G  F  T  F  S  N  Y  W  M  N  W  V  R  Q  A   -

CCAGGGAAAGGGCTGGAGTGGGTGGCCGCCATAAACCAAGATGGAAGTGAGAAATACTAT
    181 ---------+---------+---------+---------+---------+---------+  240
        GGTCCCTTTCCCGACCTCACCCACCGGCGGTATTTGGTTCTACCTTCACTCTTTATGATA
         P  G  K  G  L  E  W  V  A  A  I  N  Q  D  G  S  E  K  Y  Y   -

GTGGGCTCTGTGAAGGGCCGATTCACCATCTCCAGAGACAACGCCAAGAACTCACTGTAT
    241 ---------+---------+---------+---------+---------+---------+  300
        CACCCGAGACACTTCCCGGCTAAGTGGTAGAGGTCTCTGTTGCGGTTCTTGAGTGACATA
         V  G  S  V  K  G  R  F  T  I  S  R  D  N  A  K  N  S  L  Y   -

MV432   CTGCAAATGAACAGCCTGAGAGTCGAGGACACGGCTGTGTATTACTGTGTGAGGGACTAT
    301 ---------+---------+---------+---------+---------+---------+  360
        GACGTTTACTTGTCGGACTCTCAGCTCCTGTGCCGACACATAATGACACACTCCCTGATA
         L  Q  M  N  S  L  R  V  E  D  T  A  V  Y  Y  C  V  R  D  Y   -

TACGATATTTTGACCGATTATTACATCCACTATTGGTACTTCGATCTCTGGGGCCGTGGC
    361 ---------+---------+---------+---------+---------+---------+  420
        ATGCTATAAAACTGGCTAATAATGTAGGTGATAACCATGAAGCTAGAGACCCCGGCACCG
         Y  D  I  L  T  D  Y  Y  I  H  Y  W  Y  F  D  L  W  G  R  G   -

MV433   ACCCTGGTCACTGTCTCCTCAGCCTCCACCAAGGGCCCATCGGTCTTCCCCCTGGCACCC
    421 ---------+---------+---------+---------+---------+---------+  480
MV434   TGGGACCAGTGACAGAGGAGTCGGAGGTGGTTCCCGGGTAGCCAGAAGGGGGACCGTGGG
         T  L  V  T  V  S  S  A  S  T  K  G  P  S  V  F  P  L  A  P   -

TCCTCCAAGAGCACCTCTGGGGGCACAGCGGCCCTGGGCTGCCTGGTCAAGGACTACTTC
    481 ---------+---------+---------+---------+---------+---------+  540
        AGGAGGTTCTCGTGGAGACCCCCGTGTCGCCGGGACCCGACGGACCAGTTCCTGATGAAG
         S  S  K  S  T  S  G  G  T  A  A  L  G  C  L  V  K  D  Y  F   -
```

TABLE 3-continued

Nucleotide and amino-acid sequence of the heavy chain

```
             CCCGAACCGGTGACGGTGTCGTGGAACTCAGGCGCCCTGACCAGCGGCGTGCACACCTTC
        541 ---------+---------+---------+---------+---------+---------+  600
             GGGCTTGGCCACTGCCACAGCACCTTGAGTCCGCGGGACTGGTCGCCGCACGTGTGGAAG
              P  E  P  V  T  V  S  W  N  S  G  A  L  T  S  G  V  H  T  F  -

CCGGCTGTCCTACAGTCCTCAGGACTCTACTCCCTCAGCAGCGTGGTGACCGTGCCCTCC
        601 ---------+---------+---------+---------+---------+---------+  660
             GGCCGACAGGATGTCAGGAGTCCTGAGATGAGGGAGTCGTCGCACCACTGGCACGGGAGG
              P  A  V  L  Q  S  S  G  L  Y  S  L  S  S  V  V  T  V  P  S  -

AGCAGCTTGGGCACCCAGACCTACATCTGCAACGTGAATCACAAGCCCAGCAACACCAAG
        661 ---------+---------+---------+---------+---------+---------+  720
MV435        TCGTCGAACCCGTGGGTCTGGATGTAGACGTTGCACTTAGTGTTCGGGTCGTTGTGGTTC
              S  S  L  G  T  Q  T  Y  I  C  N  V  N  H  K  P  S  N  T  K  -

GTGGACAAGAGAGTTGAGCCCAAATCTTGTGACAAAACTCACACATGCCCACCGTGCCCA
        721 ---------+---------+---------+---------+---------+---------+  780
#265         CACCTGTTCTCTCAACTCGGGTTTAGAACACTGTTTTGAGTGTGTACGGGTGGCACGGGT
              V  D  K  R  V  E  P  K  S  C  D  K  T  H  T  C  P  P  C  P  -

TAA
        781 ---                                                             783
             ATT
```

The amino-acid sequence coding for the variable domain is bold and underlined. The oligonucleotide primers used for cloning and sequencing are indicated.

TABLE 4

(Amino acid sequences of the CDR loops):

Light-chain

| | | |
|---|---|---|
| L-CDR1 | Kabat definition | R-A-S-Q-S-V-S-S-S-Y-L-A |
| | Chothia/X-ray definition | R-A-S-Q-S-V-S-S-S-Y-L-A |
| L-CDR2 | Kabat definition | G-A-S-S-R-A-T |
| | Chothia/X-ray definition | G-A-S-S-R-A-T |
| L-CDR3 | Kabat definition | Q-Q-Y-G-S-S-P-C-T |
| | Chothia/X-ray definition | Q-Q-Y-G-S-S-P-C-T |

Heavy-chain

| | | |
|---|---|---|
| H-CDR1 | Kabat definition | N-Y-W-M-N |
| | Chothia/X-ray definition | G-F-T-F-S-N-Y-W-M-N |
| H-CDR2 | Kabat definition | A-I-N-Q-D-G-S-E-K-Y-Y-V-G-S-V-K-G |
| | Chothia/X-ray definition | A-I-N-Q-D-G-S-E-K-Y-Y |
| H-CDR3 | Kabat definition | D-Y-Y-D-I-L-T-D-Y-Y-I-H-Y-W-Y-F-D-L |
| | Chothia/X-ray definition | C-V-R-D-Y-Y-D-I-L-T-D-Y-Y-I-H-Y-W-Y-F-D-L-W-G |

Example 3

Cell proliferation assay (MTS or [$^3$H]thymidine incorporation): Cell proliferation is monitored with e.g. the CellTiter 96 AQ$_{UEOUS}$ One Solution Cell Proliferation Assay (Promega, UK). In preliminary experiments cultures of different cell lines e.g. 5 different cell lines are set up (1×10$^5$ cells/mL in tissue culture flasks) in the presence or absence of AIN457. Proliferation is assessed on aliquots taken daily from days 1 to 4 in order to establish the most representative time-point. Replicate experiments are thereafter set up by plating the cells directly into 96-well plates and staining with MTS. A minimum of 95% viability as assessed by Trypan blue staining is required for the initiation of any experiment. For each cell line 50 μl of a cell suspension in a suitable culture medium are seeded at 1×10$^5$ cells/mL into flat-bottomed wells (1×10$^4$ cells/well), to which is added 50 μl of culture medium or a 2×IL-17 binding molecule, e.g. AIN457, in a suitable culture medium. All samples are plated in quadruplicate. The plate is incubated at in a humidified, 5% CO2 atmosphere. On day 3, 20 μl of MTS reagent is added to each well, and the plate is re-incubated for a further 3-4 hours for stain development. At the end of this period, the plates are gently agitated and absorbance at 490 nm is recorded on an automatic microplate reader (MRX, Dynatech, Billingshurst, UK). Averaged blank values (no cells, no IL-17 binding molecule, e.g. AIN457) are subtracted from sample values, and these corrected A490 values are calculated as percentages of the control cultures grown in the absence of IL-17 binding molecule, e.g. AIN457. Error bars indicate the range defined in duplicate experiments, and significant differences considered as those which fell outside the region of overlap in the ranges of the means.

Example 4

Xenograft Model

Activity on xenograft models (human tumors implanted in SCID mice): Tumors are established in SCID mice by subcutaneous injection of a human tumor cell suspension derived from cultures of human tumor cells into the flank of the animal. Treatment is started once the tumors have reached a certain size (eg 150 mm$^3$), or after a certain time post cell inoculation, (eg day 4-7). The IL-17 binding molecule, e.g. AIN457 to be tested is administered i.p. or i.v. once per day (or once every 2-4 days). Antitumor activity is expressed as T/C % (mean increase in tumor volumes of treated animals divided by the mean increase of tumor volumes of control animals multiplied by 100) and % regressions (tumor volume minus initial tumor volume divided by the initial tumor volume and multiplied by 100).

Example 5

Assessment of Effect of IL-17 on Cytokine Release by Tumor Cells

Tumoral cell lines or freshly explanted tumor cells (1×10^5/ml) are cultured in RPMI 1640 containing 10% FCS, 2 mM L-glutamine, 100 IU/ml penicillin, and 100 ug/ml streptomycin with or without IL-17 (range 0.1 ng/ml to 1 ug/ml) or IL-17 plus a 10-100 fold excess of AIN457 for 48 or 72 h. Cell-free supernatants can be collected and tested immediately or stored at −70° C. for several days or even months. Concentrations of many different cytokines such as e.g. IL-6, IL-8, CXCL1, CXCL5 (but not limited to these) are measured using commercially available ELISA kits such as those of R&D Systems. PGE2 concentration can be assessed as well, using commercial sources such as the assay from Cayman Chemicals. The concentration of the measured cytokines should be significantly lower when the tumor cells are grown in the presence of an IL17 binding molecule, e.g. A1N457.

Example 6

Carcinogenesis Model

Mice are treated with 9,10-dimethyl-1,2-benzanthracene (DMBA; Sigma) in 200 ml acetone at 100 mg per mouse once at the age of 2-3 months, then treated twice-weekly with the tumour promoter 12-O-tetradecanoyl-phorbol acetate (TPA; Fisher) in 200 ml acetone, 30 ug per mouse for up to 1 year. Tumors observed arise as papillomas (keratoacanthomas) but can progress towards carcinomas and metastasize via the lymph drainage. Papilloma counts are conducted routinely by visual examination and can be evaluated statistically. The role of 11-17 is assessed by administering AIN457, e.g. 1 mg per mouse weekly, daily or every $2^{nd}$ or $3^{rd}$ day. Mice treated with an IL17 binding molecule, e.g. AIN457, should show a significantly lower incidence of papilloma and slower progression towards carcinomas and metastasis.

Example 7

Clinical Trial: A phase 1, dose-finding study of AIN457 administered once every three weeks to adult patients with advanced solid tumors.
Objectives:
 Primary: To characterize the safety profile, including both acute and cumulative toxicities, and determine the maximum tolerated dose of single agent AIN457 administered by intravenous infusion once every three weeks to adult patients with advanced solid tumors who have failed standard systemic therapy or for whom standard systemic therapy does not exist.
 Secondary: 1. To characterize the pharmacokinetics of single agent AIN457 administered by intravenous infusion once every three weeks to this population of patients; data obtained are used in concert with pharmacodynamic data to make pharmacokinetic/pharmacodynamic (PK/PD) correlations that help predict safety and efficacy
  2. To obtain preliminary evidence of antitumor activity of AIN457 administered by intravenous infusion once every three weeks to this population of patients
  3. To correlate intratumor drug levels between adult patients with advanced solid tumors receiving AIN457 by intravenous infusion once every three weeks to those associated with efficacy in preclinical models.
  4. To gather information on tumors from tumor biopsy samples where available and accessible pre- and post-therapy in order to identify biological factors that correlate with efficacy and response.
Design This is an open-label, dose-escalation study to assess the safety, pharma-cokinetics, and pharmacodynamics of AIN457 administered by intravenous infusion once every three weeks to adult patients with advanced solid tumors who have failed standard systemic therapy or for whom standard systemic therapy does not exist.
 The treatment period consists of up to six 21-day cycles. Patients experiencing unacceptable toxicity or disease progression are discontinued prematurely. Patients achieving a complete or partial response, or patients with stable disease at the end of six cycles continue further treatment according to an extension protocol at the discretion of the investigator and after approval by the sponsor. Eligible patients receive additional cycles until disease progression or unacceptable toxicity are observed.
 In the absence of dose-limiting toxicity (DLT), dose escalation proceeds as follows:
  1. First dose escalation: 100% dose increase (unless grade 2 toxicity is identified in first cohort, in which case dose escalation is 25%-67%)
  2. Dose escalations following 100% dose increase from first to second cohort: 67% dose increases until grade 2 toxicity is identified
  3. Final dose escalations following identification of grade 2 toxicity: 25%-67% dose increases, based on consensus reached among the investigators and the sponsor
 Dose escalation is based on toxicities from the first cycle for each cohort of patients. The provisional maximum tolerated dose (MTD) is defined as the dose level immediately below that at which DLT is observed in at least two out of 3-6 patients. The cohort defined as the provisional MTD then enrolls additional patients to a total of 12 to confirm the MTD through further evaluation of the safety, pharmacokinetic, and pharmacodynamic profiles of AIN457.
 Intrapatient dose escalation will not be permitted.
 All toxicities are defined according to the revised US National Cancer Institute Common Toxicity Criteria. DLTs are defined in the protocol; in general, however, the nature of a DLT is such that it is considered unacceptable even in the setting of an incurable solid tumor.
Patients

Inclusion Criteria

The following criteria must be met for inclusion into the study:
1. Male or female patients ≧18 years of age.
2. Histologically documented advanced solid tumor, who have failed standard systemic therapy and up to 1 additional systemic therapy, or for whom standard systemic therapy does not exist.
3. At least one measurable, evaluable, or non-evaluable site of disease as defined by Southwestern Oncology Group (SWOG) Solid Tumor Response Criteria including tumor marker value that is above the institutional upper limit of normal.
4. Women of childbearing potential must have a negative serum β-HCG pregnancy test prior to the initiation of study drug. Male and female patients of reproductive potential must agree to employ an effective method of birth control throughout the study and for up to 3 months following discontinuation of study drug.
5. World Health Organization (WHO) Performance Status Score of s 2.
6. Life expectancy of at least 3 months.
7. Written informed consent is obtained prior to any screening procedures.

Exclusion Criteria

Exclusion from the study is required if any of the following apply:
1. Female patients who are pregnant or breast-feeding. Postmenopausal women must be amenorrheic for at least 12 months to be considered of non-childbearing potential.
2. Patient has a severe and/or uncontrolled medical disease (i.e., uncontrolled diabetes, congestive heart failure, myocardial infarction within 6 months of study, chronic renal disease, or active uncontrolled infection).
3. Patient has a known brain metastasis.
4. Patient has an acute or known chronic liver disease (i.e., chronic active hepatitis, cirrhosis).
5. Patient has a known diagnosis of human immunodeficiency virus (HIV) infection.
6. Patient has received any investigational agent within 30 days prior to study entry.
7. Patient received chemotherapy within 4 weeks (6 weeks for nitrosoureas or mitomycin C) prior to study entry.
8. Patient received prior radiation therapy within 4 weeks prior to study entry.
9. Patient previously received radiotherapy to $\geq 25\%$ of the bone marrow.
10. Patient had a major surgery within 2 weeks prior to study entry.
11. Patient has a history of non-compliance to medical regimens.
12. Patient has impairment of hepatic, renal or hematologic function as defined by the following laboratory parameters:
   Platelet count<$100 \times 10^9$/L
   Absolute neutrophil count (ANC)<$1.5 \times 10^9$/L
   Serum ALT (SGPT) or AST (SGOT)>$2.5 \times$ institutional upper limit of normal (IULN) (>$5 \times$IULN for patients with hepatic metastases)
   Serum total bilirubin>$1.5 \times$IULN
   Serum creatinine>$1.5 \times$IULN
13. Patient is <5 years free of another primary malignancy; however, non-melanomatous skin cancer and cervical carcinoma in situ are excluded only if the patient has active disease.

Sample size This study requires about 40 patients.

Treatments AIN457 is supplied in individual 6 ml glass vials, each containing 50 mg AIN457 as lyophilized cake. Reconstitution with 1.2 mL WFI will produce a clear to opalescent, colorless; Concentrate for Solution for Infusion at a concentration of 47 mg/mL from which at least 1 mL can be removed from the vial with a standard 20 gauge needle with attached syringe. The substance is formulated in isotonic buffer (pH 5.8±0.5) containing histidine, sucrose, and Polysorbate 80 and must be diluted into 250 mL infusion bags containing 5% glucose solution before administration to patients.

The starting dose level is 0.3 mg/m². This dose is calculated as one-third of the toxic dose low (TDL) in the most sensitive species studied which, for AIN457, is the dog. Since there are no mortalities at the lower of the 2 doses administered to dogs in the GLP toxicology study—0.1 mg/kg, repeated once 3 weeks later—the TDL is estimated to be in the range of 0.05 mg/kg. Using a factor of 20 to convert mg/kg in the dog to mg/m² in humans, this starting dose is calculated as:

$$\tfrac{1}{3} \times 0.05 \text{ mg/kg} \times 20 \text{ kg/m}^2 = 0.3 \text{ mg/m}^2$$

Dose escalation proceeds according to the scheme outlined above.

The study defines treatment delays, dose reductions, or withdrawal from treatment for individuals experiencing hematologic or other toxicities known to result from AIN457. Treatment continues to a maximum of 6 cycles unless the patient experiences disease progression or unacceptable toxicity. At the end of 6 cycles, patients who have achieved a complete or partial response and patients who have had stable disease may continue further treatment according to an extension protocol at the discretion of the investigator and after approval by the sponsor.

Safety variables The safety of AIN457 assessed by physical examination and evaluation of vital signs, clinical laboratory results, adverse events, and use of concomitant medications. Adverse events are both elicited and volunteered and are graded using the revised US National Cancer Institute Common Toxicity Criteria.

Efficacy variables Although this phase 1 study is not designed to detect efficacy, activity is demonstrated as a function of the rate of objective tumor response and length of progression-free and overall survival. Baseline tumor evaluations include optimal assessment of all measurable, evaluable, and nonevaluable disease. Evaluations include physical examination and chest roentgenogram and, as appropriate, computerized tomogram of the thorax, abdomen and pelvis; sonogram of the abdomen and pelvis; bone scintigram, with bone roentgenogram of all known osseous lesions; and determination of tumor marker values. Follow-up studies are obtained every two cycles and after cessation of treatment.

Objective status is clinically evaluated using the Novartis guidelines, which are based on the SWOG response criteria. All complete and partial responses must be confirmed by a second assessment at least four weeks later. Best tumor response are calculated for each patient using the SWOG response criteria.

Pharmaco-kinetics The following pharmacokinetic parameters are calculated and analyzed for cycles 1 and 2: $t_{max}$, $C_{max}$, $\lambda_z$, $t_{1/2}$, AUC, and $R_A \cdot R_A$=the ratio of $AUC_{\tau_{cycle2}}/AUC_{\tau_{cycle1}}$ is evaluated as an index of accumulation. Preliminary assessment of dose proportionality is based on AUC from the last dose among different dose groups. PK/PD correlations with observed toxicities (e.g., hematopoietic) are performed as a predictor of safety.

Pharmaco-dynamics Tumor biopsy samples are obtained where feasible and accessible pre-therapy and after the first cycle of therapy in order to identify biological factors that correlate with efficacy and response.

Statistical methods Patients with treatment-emergent clinical adverse events (especially those with dose-limiting toxicity) or with laboratory, vital sign, or physical examination abnormalities (newly occurring or worsening from baseline) are identified and the values are flagged. The rate of abnormalities is tabulated by cohort. Objective response rates (including both complete and partial responses) are presented by cohort. Descriptive statistics are used to summarize the basic pharmacokinetic parameters by cohort.

The invention claimed is:

1. A method of treating multiple myeloma, comprising administering to a patient in need thereof a therapeutically effective amount of an IL-17 antibody or antigen binding fragment thereof comprising:
   a. a heavy ($V_H$) chain variable domain comprising the amino acid sequence set forth as SEQ ID NO:8;
   b. a light ($V_L$) chain variable domain comprising the amino acid sequence set forth as SEQ ID NO:10;
   c. a heavy ($V_H$) chain variable domain comprising the amino acid sequence set forth as SEQ ID NO:8 and a light ($V_L$) chain variable domain comprising the amino acid sequence set forth as SEQ ID NO:10; or
   d. the three Complementarity-Determining Regions (CDRs) of the amino acid sequence set forth as SEQ ID NO:8 and the three CDRs of the amino acid sequence set forth as SEQ ID NO:10.

2. The method as set forth in claim 1, wherein the three CDRs of the amino acid sequence set forth as SEQ ID NO:8 are set forth in SEQ ID NO:1, SEQ ID NO:2, and SEQ ID NO:3.

3. The method as set forth in claim 1, wherein the three CDRs of the amino acid sequence set forth as SEQ ID NO:8 are set forth in SEQ ID NO:11, SEQ ID NO:12, and SEQ ID NO:13.

4. The method as set forth in claim 1, wherein the three CDRs of the amino acid sequence set forth as SEQ ID NO:10 are set forth in SEQ ID NO:4, SEQ ID NO:5, and SEQ ID NO:6.

5. The method as set forth in claim 1, wherein the IL-17 antibody or antigen binding fragment thereof is a human antibody.

6. The method as set forth in claim 1, wherein the IL-17 antibody or antigen binding fragment thereof is a human antibody comprising the three CDRs of the amino acid sequence set forth as SEQ ID NO:8 and the three CDRs of the amino acid sequence set forth as SEQ ID NO:10.

* * * * *